(12) United States Patent
Zhang et al.

(10) Patent No.: US 7,592,309 B2
(45) Date of Patent: Sep. 22, 2009

(54) METHOD OF USING A PEPTIDE HAVING ANALGESIC AND ANTITUMOR ACTIVITY FROM SCORPION

(75) Inventors: Jinghai Zhang, Liaoning (CN); Runlin Ma, Beijing (CN); Siling Wang, Liaoning (CN); Yanfeng Liu, Liaoning (CN); Chunfu Wu, Liaoning (CN)

(73) Assignee: Shenyang Pharmaceutical University, Shenyang, Liaoning (CN)

( * ) Notice: Subject to any disclaimer, the term of this patent is extended or adjusted under 35 U.S.C. 154(b) by 99 days.

(21) Appl. No.: 10/491,077

(22) PCT Filed: Sep. 29, 2002

(86) PCT No.: PCT/CN02/00699

§ 371 (c)(1),
(2), (4) Date: Dec. 13, 2004

(87) PCT Pub. No.: WO03/037922

PCT Pub. Date: May 8, 2003

(65) Prior Publication Data

US 2006/0252676 A1     Nov. 9, 2006

(30) Foreign Application Priority Data

Sep. 30, 2001 (CN) ............................... 01 1 28235

(51) Int. Cl.
*C07K 7/00* (2006.01)
*A01N 37/18* (2006.01)

(52) U.S. Cl. ........................ 514/12; 514/2; 530/324
(58) Field of Classification Search ................ None
See application file for complete search history.

(56) References Cited

FOREIGN PATENT DOCUMENTS

CN   00112016.6   11/2001
CN   1341662 A  *  4/2002

OTHER PUBLICATIONS

Zeng (2000) Toxicon, vol. 38, p. 893-899.*
Gong et al. (1997, The Journal of Biological Chemistry, vol. 272, p. 8320-8324).*
Foucart et al. (1994) Can J Physiol Pharmacol, vol. 72, 855-861.*
Lai et al., The expression of analgesic-antitumor peptide (AGAP) from Chinese Buthus martensii Karsch in transgenic tobacco and tomato, Mol. Biol. Rep., E. publication date of Jun. 11, 2008 ahead of print; no volume # and page numbers.*
Zhu et al., Nine novel precursors to *Buthus martensii* scorpion α-toxin homologues, Toxicon 38(12), 1653-1661, 2000.
Zeng et al., Cloning and characterization of the cDNA sequences of two venom peptides from Chinese scorpion *Buthus martensii* Karsch (BmK), Toxicon 38(7), 893-899, 2000.

* cited by examiner

*Primary Examiner*—Rebecca E Prouty
*Assistant Examiner*—Alexander D Kim
(74) *Attorney, Agent, or Firm*—Westman, Champlin & Kelly, P.A.; Z. Peter Sawicki

(57) ABSTRACT

The present invention relates to a peptide having analgesic and antitumor activity derived from the scorpion and partial fragment, derivative or analogue thereof having analgesic and antitumor activity, and preparation method and use thereof. The peptide having analgesic and antitumor activity is obtained by extraction, isolation and purification from the scorpion or scorpion venom. The peptide having analgesic and antitumor activity derived from the scorpion and partial fragment, derivative or analogue thereof can be obtained by chemical synthesis method or bioengineering method. The peptide having analgesic and antitumor activity derived from the scorpion and partial fragment, derivative or analogue thereof is used as the analgesic and antitumor drugs.

3 Claims, No Drawings

METHOD OF USING A PEPTIDE HAVING ANALGESIC AND ANTITUMOR ACTIVITY FROM SCORPION

CROSS-REFERENCE TO RELATED APPLICATION

This Application is a Section 371 National Stage Application of International Application No. PCT/CN02/00699, filed 29 Sep. 2002 and published as WO 03/037922 on May 8, 2003 filed as Chinese application number 01128235.5 on 30 Sep. 2001, the content of which is hereby incorporated by reference in its entirety.

FIELD OF THE INVENTION

The present invention relates to the field of biomedicine technology. In particularly, the present invention provides a peptide having analgesic and antitumor activity from scorpion and the method for preparing thereof.

BACKGROUND OF THE INVENTION

Scorpion is also named as quan chong scorpion and quan xie scorpion, whose pharmacological property is described in detail in the traditional medical famous works such as "shi jing", "kai bao ben cao" and "ben cao gang mu", and so on. Scorpion has the function of dispelling rheumatism, calming affright, activate the channels, alleviating pains, attacking toxin and dispersing, which is used to treat febrile convulsion, convulsion, stroke, hemiplegia, rheumatism, hemicrania, headache, neuralgia, body pain, tumefaction and various kinds of malignancies. However, it is not clear which component in scorpion plays the function of activate the channels, relieving pains, attacking toxin and dispersing.

DISCLOSURE OF THE INVENTION

The peptide having analgesic and antitumor activity according to the present invention is screened, isolated, purified, found and obtained by biotechnology from scorpion or scorpion venom. The peptide having analgesic and antitumor activity not only can be purified and prepared from scorpion or scorpion venom, but also can be expressed and obtained by recombinant DNA technology, namely gene engineering method. The peptide having analgesic and antitumor activity also can be obtained by chemical synthesis method. The peptide has a significant biological activity of analgesic and antitumor.

The present invention provides a peptide having analgesic and antitumor activity derived from scorpion, wherein the amino acid sequence of the peptide is shown as SEQ ID NO: 1. The present invention also provides partial fragment, derivative or analogue of the peptide having analgesic and antitumor activity, wherein the partial fragment or analogue or derivative is obtained by deleting the partial amino acids of N terminal or C terminal of the peptide, or by substituting, adding or deleting one or more amino acids or the partial amino acids in the extended part of N terminal or C terminal of the peptide. In one embodiment, the present invention provides an analogue of the peptide having analgesic and antitumor activity, wherein the amino acid sequence is shown as SEQ ID NO: 3. In another embodiment, the present invention provides a derivative of the peptide having analgesic and antitumor activity, wherein the amino acid sequence is shown as SEQ ID NO: 4.

The present invention also provides a polynucleotide acid encoding the said peptide or partial fragment, derivative or analogue thereof having analgesic and antitumor activity, wherein the sequence of polynucleotide acid encoding the said peptide is shown as SEQ ID NO: 2.

The present invention provides a method for the preparation of the peptide having analgesic and antitumor activity derived from scorpion, which is isolated from the scorpion or scorpion venom, comprising the following steps:

(1) extracting scorpion or scorpion venom with distilled water, acidic solution and basic solution, respectively, then centrifuging to remove the impunity, (2) performing hydrophobic chromatography of the extract to give the active ingredient having analgesic and antitumor activity, (3) ultra-filtrating the active ingredient having analgesic and antitumor activity to remove salt and impurity proteins, concentrating, purifying the active ingredient having analgesic and antitumor activity by cation exchange chromatography, (4) further purifying the active ingredient having analgesic and antitumor activity by hydrophobic chromatography, (5) desalting by ultra-filtration and concentrating, and purifying by gel filtration chromatography to give electrophoresis pure active ingredient having analgesic and antitumor activity, (6) further purifying the active ingredient having analgesic and antitumor activity by reverse phase column chromatography.

According to one preferred embodiment of the present invention, wherein in step (1), the scorpion venom is extracted by distilled water, then the extract is extracted by the acidic solution with a pH of 2 or more, and the basic solution with a pH of 12 or less to remove the impunity;

in step (2), hydrophobic chromatography is performed twice, wherein the chromatography medium is phenyl-, octane- or butyl-hydrophobic chromatography medium, the pH of sodium phosphate eluent is physiologically acceptable, wherein the concentration of phosphate radical is 5 mM-100 mM, and the gradient of concentration of $(NH_4)_2SO_4$ or $Na_2SO_4$ is 2.0M-0.0M;

in step (3) and (5), the trapped molecular weight of ultra-filtration membrane is 30 kDa or 1 kDa;

in step (5), the medium of gel filtration chromatography is chromatographic filler Sephacryl S-100 Hr, Superose 6 prep grade, Superose 12 prep grade, Superdex 30 prep grade, or Superdex 75 prep grade, and the pH of eluent is in a range of between 2 and 12;

in step (6), the medium of reverse phase chromatography is chromatographic filler SOURCE 15RPC or SOURCE 30RPC, the eluent is 0.1% trifluoroacetic acid-acetonitrile aqueous solution, and the gradient of concentration of acetonitrile is from 20% to 95%; the whole process including extraction, isolation and purification is performed in the half-sterile or sterile room at 10° C.-30° C.

According to another preferred embodiment of the present invention, wherein in step (1), the scorpion is homogenized and extracted by distilled water, then the extract is extracted by the acidic solution with a pH of 2 or more, and the basic solution with a pH of 12 or less to remove the impunity;

in step (2), hydrophobic chromatography is performed twice, wherein the chromatography medium is phenyl-, octane- or butyl-hydrophobic chromatography medium, the pH of sodium phosphate eluent is physiologically acceptable, wherein the concentration of phosphate radical is 5 mM-100 mM, and the gradient of concentration of $(NH_4)_2SO_4$ or $Na_2SO_4$ is 2.0M-0.0M;

in step (3) and (5), the trapped molecular weight of ultrafiltration membrane is 30 kDa or 1 kDa;

in step (5), the medium of gel filtration chromatography is chromatographic filler Sephacryl S-100 Hr, Superose 6 prep grade, Superose 12 prep grade, Superdex 30 prep grade, or Superdex 75 prep grade, and the pH of eluent is in a range of between 2 and 12;

in step (6), the medium of reverse phase chromatography is chromatographic filler SOURCE 15RPC or SOURCE 30RPC, the eluent is 0.1% trifluoroacetic acid-acetonitrile aqueous solution, and the gradient of concentration of acetonitrile is from 20% to 95%; the whole process including extraction, isolation and purification is performed in the half-sterile or sterile room at 10° C.-30° C.

The present invention also provides a method for the preparation of the peptide or partial fragment, derivative or analogue thereof having analgesic and antitumor activity according to the present invention, which is synthesized, processed, purified and prepared by chemical synthesis method.

The present invention further provides a method for the preparation of the peptide or partial fragment, derivative or analogue thereof having analgesic and antitumor activity according to the present invention, which is expressed, processed, purified and prepared by recombinant DNA technology.

The present invention also provides use of the peptide or partial fragment, derivative or analogue thereof having analgesic and antitumor activity in the preparation of analgesic medicament. The present invention further provides use of the peptide or partial fragment, derivative or analogue thereof having analgesic and antitumor activity in the preparation of antitumor medicament.

The present invention is achieved by the following technical schemes:

According to the differences in molecular weight, isoelectric point, the hydrophobic properties of molecular surface between the peptide having analgesic and antitumor activity derived from the scorpion or scorpion venom and other proteins, polypeptide, or enzymes, the peptide having analgesic and antitumor activity derived from the scorpion, wherein the amino acid sequence is shown as SEQ ID NO: 1, is extracted, purified and obtained from the scorpion or scorpion venom by ultra filtration, gel filtration chromatography, ion exchange chromatography, hydrophobic chromatography and reverse phase chromatography. The extraction, isolation and purification processes of the peptide having analgesic and antitumor activity are performed in the half-sterile or sterile room at 10° C.-30° C. According to the structure of the active peptide, the peptide or the partial fragment thereof or derivative or analogue thereof having analgesic and antitumor activity is obtained by the chemical synthesis method. According to the structure of the active peptide, the gene of the peptide or the partial fragment thereof or derivative or analogue thereof having analgesic and antitumor activity is obtained by the chemical synthesis method or biotechnology. The gene is cloned into an engineering expression vector by recombinant DNA technology, i.e. gene engineering method. The peptide or the partial fragment thereof or derivative or analogue thereof having analgesic and antitumor activity is obtained by expression and purification.

The peptide having analgesic and antitumor activity from scorpion according to the present invention can be prepared into various kinds of conventional formulations according to the traditional preparation technology in the field. The example of formulation is injectable formulation, such as intravenous injection and intramuscular injection, oral administration formulation. The oral administration formulation should be a formulation that can not be degraded by pepsin, such as inclusions. The administration amount is determined according to the administration route, the condition of the subject and other factors. Typically, for adults with about 70 Kg weight, preferably the dose is about 0.01-100 mg/kg weight. When required, the upper limit of dose can be exceeded.

The peptide or the partial fragment thereof or derivative or analogue thereof having analgesic and antitumor activity according to the present invention not only can be used as the drug for treating various kinds of pains and tumor diseases, but also can be used as the research tool to screen the new analgesic and antitumor compounds.

The method for the preparation of the peptide or the partial fragment thereof or derivative or analogue thereof having analgesic and antitumor activity has the advantage of simple and high yield, which has guide significance and utility value to research and develop a new analgesic and antitumor medicine, and establishes a basis of industrialization production.

EXAMPLES

Example 1

2.0 g of scorpion venom was dissolved into 20 ml distilled water, centrifuged at 15000 rpm/min for 15 min, the supernatant was adjusted to pH 2 with 0.01M HCl or phosphoric acid and centrifuged at 15000 rpm/min for 15 min, then the supernatant was adjusted to pH 12 using sodium phosphate and centrifuged at 15000 rpm/min for 15 min. The pH of supernatant was adjusted to physiologically acceptable pH with HCl or phosphoric acid, $(NH_4)_2SO_4$ or $Na_2SO_4$ was added to the concentration of 2M, then loaded onto the hydrophobic chromatography column (2.6cm×30cm), such as phenyl- or octane-hydrophobic chromatography column, balanced with 2M $(NH_4)_2SO_4$ or $Na_2SO_4$ solution in advance, then eluted with 1.5M, 1.0M and 0.5M $(NH_4)_2SO_4$ or $Na_2SO_4$ buffers respectively, finally eluted with 50mM sodium phosphate buffer (pH was adjusted to physiologically acceptable pH). The elution solutions containing the analgesic and antitumor active ingredients were combined, then performed ultra filtration using the ultra-filtration membranes with trapped the molecular weight of 30 kDa (kilo Daltons) and 1 kDa respectively to remove the salts and impurity proteins in the elution solution, finally balanced with 10mM pH4.0 citric acid-sodium phosphate. Then the balanced ultra-filtration sample in the range of 30 kDa and 1 kDa (kilo Daltons) was loaded onto the cation exchange column (2.6 cm×50 cm), such as CM- and SP-cation exchange chromatography column, balanced with 10 mM pH4.0 citric acid-sodium phosphate buffer in advance. At first the column was thoroughly washed with 10 mM pH4.0 citric acid-sodium phosphate buffer, then performed gradient elution of NaCl solution (0.0M-1.0M) by using 10mM pH4.0 citric acid-sodium phosphate buffer as the basic buffer. The elution solutions containing the analgesic and antitumor active ingredients were combined, adjusted pH to physiologically acceptable pH with NaOH or HCl or phosphoric acid, then $(NH_4)_2SO_4$ or $Na_2SO_4$ was added to 2.0M, loaded onto the hydrophobic chromatography column (2.6 cm×30 cm), such as butyl- or octane-hydrophobic chromatography column, balanced with 2 M $(NH_4)_2SO_4$ or $Na_2SO_4$ solution in advance, then performed gradient elution of the neutralized salt (2.0M-0.0M) by using 50 mM sodium phosphate (pH was adjusted to physiologically acceptable pH) as the basic solution. The second peak of two eluting peaks was combined and collected, ultra-filtrated with the ultra-filtration membrane of the trapped molecular weight of 1 kDa (kilo Daltons), the sample was loaded onto the gel filtration chromatography column (1.6 cm×60 cm), such as Sephacryl S-100 Hr or Superose6, 12prep grade or Superdex30, 75prep grade chromatography column, balanced with 20 mM sodium phosphate (pH was adjusted to physiologically acceptable pH, containing 150 mM NaCl) in advance. The peak ingredients with the largest eluting peak area were combined and collected, the ingredient was a single silver-stained band in SDS-PAGE, the active ingredient obtained in gel filtration chromatography was loaded onto the reverse phase column (1.0 cm×15 cm), such as SURCE 15RPC and 30PRC chromatography column, balanced with 0.1% trifluoroacetic acid-20% acetonitrile aqueous solution in advance. At first, the column was thoroughly washed with 0.1% trifluoroacetic acid-20% acetonitrile aqueous solution, then performed gradient elution with acetonitrile (20% to 95%). The peak ingredients with the largest eluting peak area were combined and collected. The eluting peak area of the ingredient was more than 95% of the whole eluting peak area of the reverse phase chromatography. The ingredient was collected and dried in vacuum at the temperature lower than 30° C. (lyophylization in vacuum also can be used). The traditional reducing agent was used to open and protect the disulfide bond of the peptide having analgesic and antitumor activity derived from scorpion. The N-terminal amino acid sequence of the peptide was determined according to Edman degradation method by applying the protein sequencer of Applied Biosystems. The C-terminal amino acid sequence of the peptide was determined by carboxypeptidase Y degradation method. The amino acid sequence of the peptide having analgesic and antitumor activity derived from scorpion was shown as SEQ ID NO: 1.

Example 2

1000 g scorpion was homogenized by adding 2.5L distilled water, and centrifuged at 4500 rpm/min for 20 min. The supernatant was collected. The precipitate was homogenized by adding 1.5L of distilled water, and centrifuged at 4500 rpm/min for 20 min. The supernatant was collected. The precipitate was homogenized by adding 1.0L of distilled water, and centrifuged at 4500 rpm/min for 20 min. The supernatant was collected, the extracts of the above three times was combined and adjusted pH to 2 using 0.01M HCl or phosphoric acid, centrifuged at 5000 rpm/min for 15 min. The supernatant was collected and adjusted pH to 12 using sodium phosphate, then centrifuged at 5000 rpm/min for 15 min. Other processes were the same as those in Example 1.

Example 3

The fragment of nucleic acid was synthesized according to the amino acid sequence of the peptide having analgesic and antitumor activity derived from scorpion (the amino acid sequence was shown as SEQ ID NO: 1). The full-length gene of the peptide or the gene fragment of the derivative or analogue thereof or the partial gene fragments thereof having analgesic and antitumor activity were screened by hybridization from the scorpion cDNA pool or cDNA library or DNA library. For example, the full-length gene sequence of the peptide derived from the breeding scorpion was shown as SEQ ID NO: 2. The full-length gene sequence of peptide derived from the wild scorpion was identical with that from breeding scorpion except that the codons encoding the amino acids of position 24 and position 29 were GAC and AAT respectively.

Example 4

The PCR degenerate primers were designed according to the amino acid sequence of N-terminal or C-terminal of the peptide having analgesic and antitumor activity derived from scorpion. Primer 1 shown as SEQ ID NO: 5 contained nucleotide sequence (residues 1-15 of SEQ ID NO: 2) encoding the amino acids of position 1-5 of the peptide in SEQ ID NO: 1. Primer 2 shown as SEQ ID NO: 6 contained the complementary strand of nucleotide sequence (residues 181-198 of SEQ NO: 2 ) encoding the amino acids of position 61-66 of the peptide in SEQ ID NO: 1. The analogue of the recombinant peptide was obtained from these two primers, wherein the amino acid sequence was shown as SEQ ID NO:3. Primer 3 shown as SEQ ID NO. 7 contained nucleotide sequence (residues 1-15 of SEQ ID NO: 2) encoding the amino acids of position 1-5 of the peptide in SEQ ID NO: 1. Primer 4 shown as SEQ ID NO: 8 contained the complementary strand of nucleotide sequence (residues 181-198 of SEQ ID NO: 2) encoding the amino acids of position 61-66 of the peptide in SEQ ID NO: 1. The derivative of the recombinant peptide was obtained from these two primers, wherein the amino acid sequence was shown as SEQ ID NO: 4. The full-length gene fragments thereof having analgesic and antitumor activity were screened from cDNA pool or cDNA library or DNA library by PCR reaction.

Example 5

The full-length gene of the peptide or the gene fragment of the derivative or analogue thereof or the partial gene fragments thereof were synthesized according to the structure (amino acid sequence) of the peptide or partial fragment, derivative or analogue thereof having analgesic and antitumor activity shown as SEQ ID NO:1, 3 and 4 in the specification.

Example 6

The genes obtained in Example 3, 4 and 5 were digested by restricted endoenzymes and cloned into various kinds of the engineering expression vectors. For example, the obtained PCR products in Example 4 were digested by restricted endoenzymes NcoI/XhoI or by NdeI/BamHI and cloned into the E.coli expression vector pET28a. The recombinant peptide or the extended or shorted derivative or analogue thereof (the amino acid sequences were shown as SEQ ID NO: 3 and 4) were obtained by expression, post-process, isolation and purification.

Example 7

The mouse with acetic acid writhing model was administrated intravenously with the peptide derived from the scorpion or partial fragment, derivative or analogue thereof having analgesic and antitumor activity obtained in Example 1, 2 and 6 in a dose of 0.1 mg/kg weight to 16.0 mg/kg weight. The inhibitory rate of writhing response of mouse was 0.0% to 100%. For example, the $ED_{50}$ (median effective dose) of the peptide of the SDS-PAGE single band obtained in Example 1 was 0.47 mg/kg weight, the $ED_{50}$ (median effective dose) of morphine by intravenous administration as the positive control was 16.0 mg/kg weight. The above samples were administrated by stomach infusion in a dose of 0.1 mg/kg weight to 16.0 mg/kg weight. The inhibitory rate of writhing response of mouse was 0.0% to 100%. For example, the $ED_{50}$ (median effective dose) of the peptide of the SDS-PAGE single band obtained in Example 2 was 2.86mg/kg weight. In the mouse heat plate model, the above samples were administrated by intravenous injection in a dose of 0.1 mg/kg weight to 16.0 mg/kg weight. The threshold value of pain of the mouse (the time required to lick the back foot on the heat plate of 55° C.±5° C.) was the normal value (from 10 seconds to 30 seconds) to 60 seconds (if the pain threshold value was more than 60 seconds, the mouse did not lick the back foot yet, then the mouse was taken out). For example, the peptide of SDS-PAGE single band obtained in example 1 and 2 were injected intravenously at 0.6 mg/kg weight. The pain threshold were raised in a rate of 16.5%, 145.7%, 219.1%, 219.1%, 177.6%, 32.4%, 14.9% at 5 min, 15 min, 25 min, 35 min, 45 min, 60 min and 90 min respectively. When morphine was administrated intravenously in a dose of 10.0 mg/kg weight, the pain threshold were raised in a rate of 0.6%, 27.0%, 112.6%, 177.9%, 125.8%, 50.9% and −3.7% at 5 min, 15 min, 25 min, 35 min, 45 min, 60 min and 90 min respectively.

Example 8

In mouse experimental tumor model, such as ehrlich ascites carcinoma and S180 entity tumor, the peptide derived from the scorpion or partial fragment, derivative or analogue thereof having analgesic and antitumor activity obtained in example 1,2 and 6 was injected subcutaneously in a dose of 0.1 mg/kg weight to 16.0 mg/kg weight for continuous seven days. The inhibitory rate of tumor weight of S180 sarcoma solid tumor [(C-T)/C, wherein C was the average tumor weight of the control group and T was the average tumor weight of the test group] was 0% to 62%. For example, the peptide of the SDS-PAGE single band obtained in Example 1 was administrated at the dose of 0.639 mg/kg weight. The inhibitory rate of tumor weight was 30.9%. The inhibitory rate of tumor weight was 50.5% when cyclophosphamide was used as the positive control in the dose was 60.0 mg/kg weight. The peptide derived from the scorpion or partial fragment, derivative or analogue thereof having analgesic and antitumor activity obtained in example 1,2 and 6 was administrated by stomach infusion in a dose of 0.1 mg/kg weight to 16.0 mg/kg weight for continuous ten days. The rate of life prolonging of mouse with ehrlich ascites carcinoma were 0% to 46%. For example, the rate of life prolonging of the peptide of the SDS-PAGE single band obtained in Example 2 were 16.8% and 31.5% in the dose of 0.213 mg/kg weight and 0.639 mg/kg weight respectively. For the cyclophosphamide as the positive control, the rate of life prolonging was 15.6% in a dose of 60.0 mg/kg weight (administration by subcutaneous injection).

What is claimed is:

1. A method comprising the steps of isolating and purifying a peptide consisting of the amino acid sequence of SEQ ID NO: 1, the peptide analogue thereof consisting of the amino acid sequence of SEQ ID NO: 3 or the peptide derivative thereof consisting of the amino acid sequence of SEQ ID NO: 4, and administering a composition comprising said peptide, said peptide derivative or said peptide analogue to a patient; wherein the step of administering reduces pain or inhibits tumor growth in the patient.

2. A method comprising the steps of preparing a peptide consisting of the amino acid sequence of SEQ ID NO: 1, the peptide analogue thereof consisting of the amino acid sequence of SEQ ID NO: 3 or the peptide derivative thereof consisting of the amino acid sequence of SEQ ID NO: 4 by recombinant DNA technology, and administering a composition comprising said peptide, said peptide derivative or said peptide analogue to a patient; wherein the step of administering reduces pain or inhibits tumor growth in the patient.

3. A method comprising the steps of obtaining a peptide consisting of the amino acid sequence of SEQ ID NO: 1, the peptide analogue thereof consisting of the amino acid sequence of SEQ ID NO: 3 or the peptide derivative thereof consisting of the amino acid sequence of SEQ ID NO: 4 by chemical synthesis, and administering a composition comprising said peptide, said peptide derivative or said peptide analogue to a patient; wherein the step of administering reduces pain or inhibits tumor growth in the patient.

* * * * *

UNITED STATES PATENT AND TRADEMARK OFFICE
CERTIFICATE OF CORRECTION

PATENT NO. : 7,592,309 B2  Page 1 of 1
APPLICATION NO. : 10/491077
DATED : September 22, 2009
INVENTOR(S) : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 451 days.

Signed and Sealed this

Twenty-first Day of September, 2010

David J. Kappos
*Director of the United States Patent and Trademark Office*

SEQUENCE LISTING

<160> NUMBER OF SEQ ID NOS: 8

<210> SEQ ID NO 1
<211> LENGTH: 66
<212> TYPE: PRT
<213> ORGANISM: Scorpion

<400> SEQUENCE: 1

```
Val Arg Asp Gly Tyr Ile Ala Asp Asp Lys Asn Cys Ala Tyr Phe Cys
1               5                   10                  15

Gly Arg Asn Ala Tyr Cys Asp Asp Glu Cys Lys Lys Asn Gly Ala Glu
            20                  25                  30

Ser Gly Tyr Cys Gln Trp Ala Gly Val Tyr Gly Asn Ala Cys Trp Cys
        35                  40                  45

Tyr Lys Leu Pro Asp Lys Val Pro Ile Arg Val Pro Gly Lys Cys Asn
    50                  55                  60

Gly Gly
65
```

<210> SEQ ID NO 2
<211> LENGTH: 198
<212> TYPE: DNA
<213> ORGANISM: Scorpion

<400> SEQUENCE: 2

```
gtacgcgatg gttatattgc cgacgataaa aattgcgcat atttttgtgg tagaaatgcg      60
tattgcgatg atgaatgtaa gaagaacggt gctgagagtg gctattgcca atgggcaggt     120
gtatacggaa acgcctgctg gtgctataaa ttgcccgata aagtacctat tagagtacca     180
ggaaaatgca atggcggt                                                    198
```

<210> SEQ ID NO 3

```
<211> LENGTH: 86
<212> TYPE: PRT
<213> ORGANISM: Scorpion

<400> SEQUENCE: 3
```

Met Gly Ser Ser His His His His His Ser Ser Gly Leu Val Pro
1               5                   10                  15

Gly Ser His Met Val Arg Asp Gly Tyr Ile Ala Asp Asp Lys Asn Cys
            20                  25                  30

Ala Tyr Phe Cys Gly Arg Asn Ala Tyr Cys Asp Asp Glu Cys Lys Lys
        35                  40                  45

Asn Gly Ala Glu Ser Gly Tyr Cys Gln Trp Ala Gly Val Tyr Gly Asn
    50                  55                  60

Ala Cys Trp Cys Tyr Lys Leu Pro Asp Lys Val Pro Ile Arg Val Pro
65                  70                  75                  80

Gly Lys Cys Asn Gly Gly
                85

```
<210> SEQ ID NO 4
<211> LENGTH: 75
<212> TYPE: PRT
<213> ORGANISM: Scorpion

<400> SEQUENCE: 4
```

Met Val Arg Asp Gly Tyr Ile Ala Asp Asp Lys Asn Cys Ala Tyr Phe
1               5                   10                  15

Cys Gly Arg Asn Ala Tyr Cys Asp Asp Glu Cys Lys Lys Asn Gly Ala
            20                  25                  30

Glu Ser Gly Tyr Cys Gln Trp Ala Gly Val Tyr Gly Asn Ala Cys Trp
        35                  40                  45

Cys Tyr Lys Leu Pro Asp Lys Val Pro Ile Arg Val Pro Gly Lys Cys
    50                  55                  60

Asn Gly Gly Leu Glu His His His His His
65                  70                  75

```
<210> SEQ ID NO 5
<211> LENGTH: 28
<212> TYPE: DNA
<213> ORGANISM: Scorpion

<400> SEQUENCE: 5
ggaattccat ggtacgcgat ggttatat                                    28

<210> SEQ ID NO 6
<211> LENGTH: 27
<212> TYPE: DNA
<213> ORGANISM: Scorpion

<400> SEQUENCE: 6
ttgctcgaga ccgccattgc attttgg                                     27

<210> SEQ ID NO 7
<211> LENGTH: 27
<212> TYPE: DNA
<213> ORGANISM: Scorpion

<400> SEQUENCE: 7
caagcatatg gtacgcgatg gttatat                                     27

<210> SEQ ID NO 8
```

```
-continued

<211> LENGTH: 33
<212> TYPE: DNA
<213> ORGANISM: Scorpion

<400> SEQUENCE: 8
ataggatcct aattaaccgc cattgcattt tgg                            33
```